(12) United States Patent
Li et al.

(10) Patent No.: US 12,349,907 B2
(45) Date of Patent: Jul. 8, 2025

(54) STAPLER RELOADS WITH CABLE-DRIVEN DRIVE BEAMS

(71) Applicant: Covidien LP, Mansfield, MA (US)

(72) Inventors: Shouwei Li, Shanghai (CN); Li Xiang, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/558,794

(22) PCT Filed: May 12, 2021

(86) PCT No.: PCT/CN2021/093335
§ 371 (c)(1),
(2) Date: Nov. 3, 2023

(87) PCT Pub. No.: WO2022/236733
PCT Pub. Date: Nov. 17, 2022

(65) Prior Publication Data
US 2024/0225646 A1 Jul. 11, 2024

(51) Int. Cl.
*A61B 17/072* (2006.01)
*A61B 34/00* (2016.01)

(52) U.S. Cl.
CPC ........ *A61B 17/07207* (2013.01); *A61B 34/71* (2016.02); *A61B 2017/07257* (2013.01); *A61B 2017/07271* (2013.01)

(58) Field of Classification Search
CPC .......................... A61B 17/068; A61B 17/07207
USPC ...................................................... 227/175.1
See application file for complete search history.

(56) References Cited

U.S. PATENT DOCUMENTS

| 5,915,616 | A  | 6/1999  | Viola et al.   |
|-----------|----|---------|----------------|
| 5,964,394 | A  | 10/1999 | Robertson      |
| 7,128,253 | B2 | 10/2006 | Mastri et al.  |
| 7,334,717 | B2 | 2/2008  | Rethy et al.   |
| 7,770,774 | B2 | 8/2010  | Mastri et al.  |
| 7,819,896 | B2 | 10/2010 | Racenet        |
| 8,070,033 | B2 | 12/2011 | Milliman et al.|
| 8,157,152 | B2 | 4/2012  | Holsten et al. |
| 8,256,656 | B2 | 9/2012  | Milliman et al.|
| 8,806,973 | B2 | 8/2014  | Ross et al.    |
| 9,713,470 | B2 | 7/2017  | Scirica et al. |

(Continued)

FOREIGN PATENT DOCUMENTS

| CN | 101273911 A | 10/2008 |
|----|-------------|---------|
| CN | 104042271 A | 9/2014  |

(Continued)

OTHER PUBLICATIONS

Extended European Search Report for European Patent Application No. 21941308.5 mailed Dec. 12, 2024, 7 pages.

(Continued)

*Primary Examiner* — Michelle Lopez

(57) ABSTRACT

A reload for a surgical stapling apparatus includes a shaft assembly and an end effector secured to the shaft assembly. The end effector includes an anvil assembly, a cartridge assembly, and a firing assembly including a drive beam and a carriage, the drive beam and the carriage coupled together by a firing cable and a retraction cable that move the drive beam through the end effector as the carriage moves through the shaft assembly.

18 Claims, 11 Drawing Sheets

(56) References Cited

U.S. PATENT DOCUMENTS

| | | | |
|---|---|---|---|
| 2008/0308604 A1* | 12/2008 | Timm | A61B 17/07207 227/180.1 |
| 2012/0018326 A1* | 1/2012 | Racenet | A61B 17/07207 206/339 |
| 2012/0116416 A1 | 5/2012 | Neff et al. | |
| 2013/0098966 A1 | 4/2013 | Kostrzewski et al. | |
| 2014/0276932 A1 | 9/2014 | Williams et al. | |
| 2016/0015391 A1 | 1/2016 | Shelton, IV et al. | |
| 2017/0265954 A1* | 9/2017 | Burbank | A61B 34/37 |
| 2019/0388089 A1 | 12/2019 | Williams | |

FOREIGN PATENT DOCUMENTS

| | | |
|---|---|---|
| CN | 108882934 B | 9/2021 |
| WO | 2016025132 A1 | 2/2016 |

OTHER PUBLICATIONS

International Search Report for Application No. PCT/CN2021/093335 dated Feb. 10, 2022.
Written Opinion for Application No. PCT/CN2021/093335 dated Feb. 10, 2022.

* cited by examiner

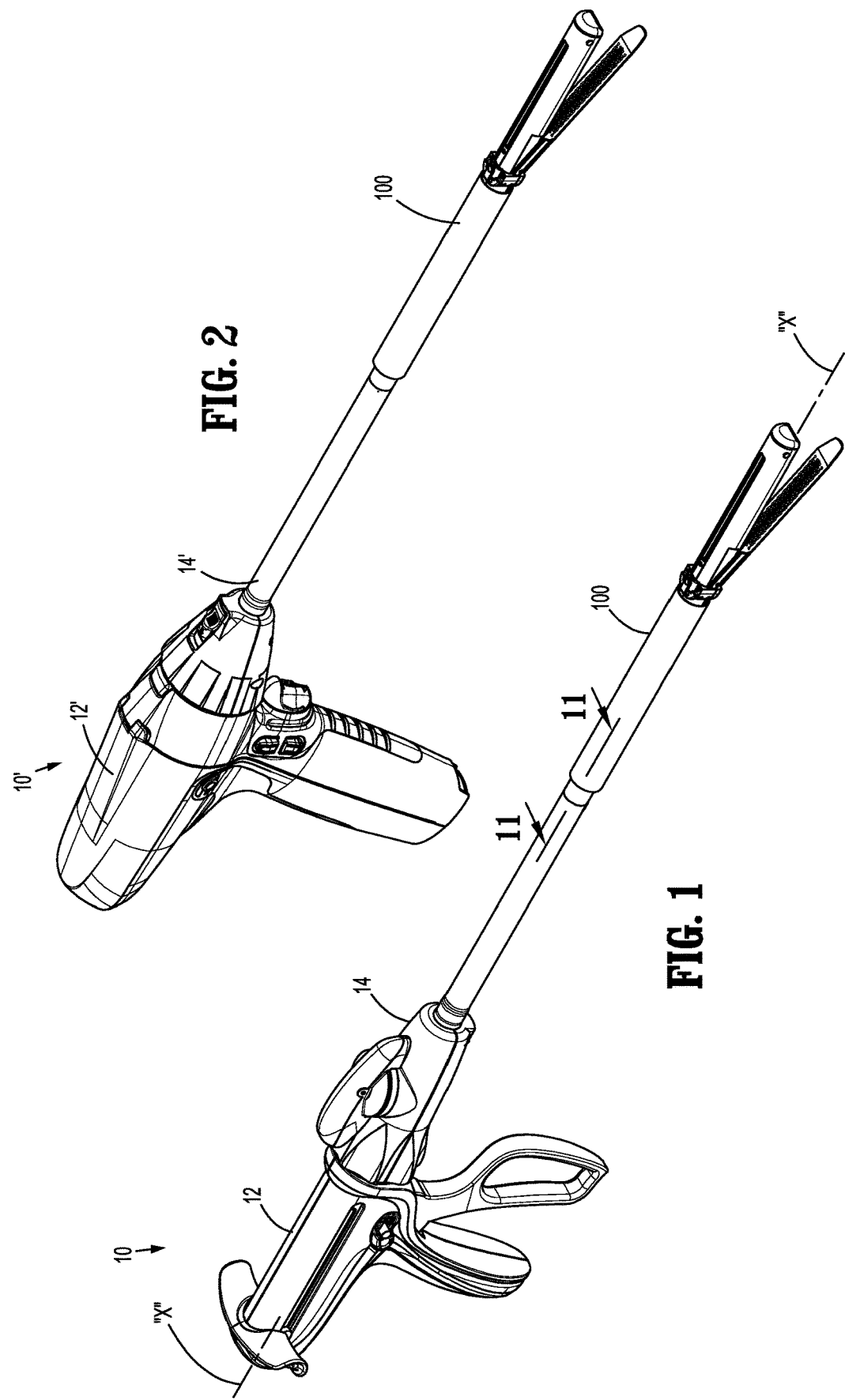

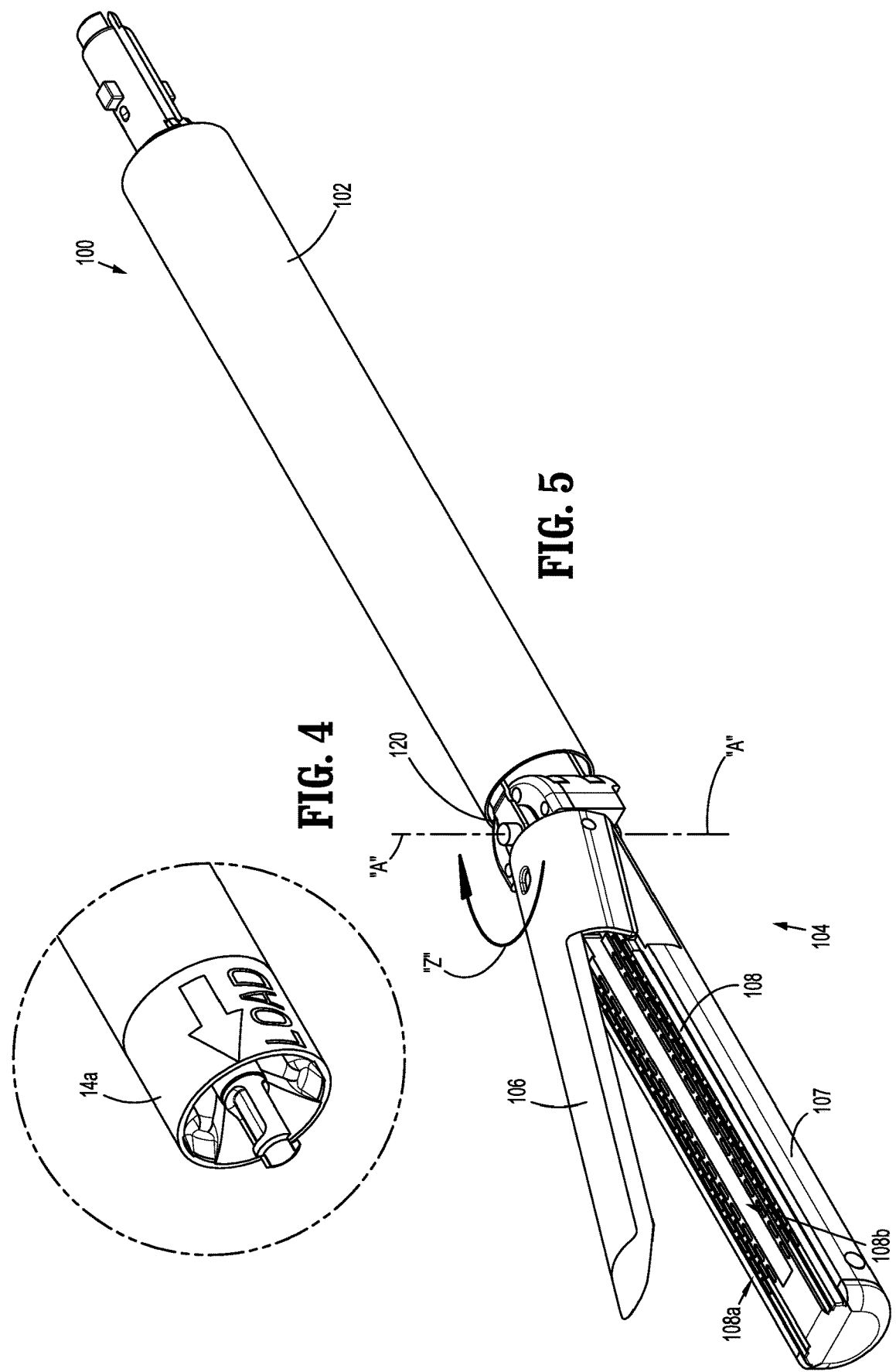

STAPLER RELOADS WITH CABLE-DRIVEN DRIVE BEAMS

TECHNICAL FIELD

This disclosure relates to surgical stapling apparatus, devices and/or systems for performing surgical procedures and methods of use thereof.

BACKGROUND

Surgical stapling apparatus that clamp, cut and/or staple tissue are well known in the art. Such surgical stapling apparatus include end effectors having two elongated jaw members used to capture or clamp tissue. One of the two jaw members usually carries a staple cartridge that houses a plurality of staples positioned in rows, while the other of the two jaw members has an anvil for forming the staples as the staples are driven from the staple cartridge. For instance, in linear surgical stapling apparatus, a stapling operation is effectuated by a cam bar, a drive sled or other similar mechanism having a cam member that travels longitudinally through channels defined in the staple cartridge and acts upon staple pushers in the channels to sequentially eject linear rows of staples from the staple cartridge. A knife, often supported on a rod-driven drive beam, is movably positioned between the linear rows of staples such that when the surgical stapling apparatus is positioned about tissue and actuated, the tissue is joined and/or simultaneously or nearly simultaneously cut.

Some surgical stapling apparatus include reloads (sometimes referred to as loading units) and handle assemblies. The reloads may include articulatable end effectors with various articulation angles relative to the handle assemblies. For instance, in surgical stapling apparatus that include rod-driven drive beams, the maximum articulation angle is typically 45 degrees. Certain surgical stapling apparatus may have a maximum articulation angle of 60 degrees, but the firing force in these surgical stapling apparatus with 60-degree articulation compared to the surgical stapling apparatus with the 45-degree articulation is substantially higher. Increased articulation angle can provide more flexibility to surgeons, particularly in surgical procedures such as low anterior resection (LAR), but the increased firing force requirements for achieving the increased articulation provides added challenges.

SUMMARY

This disclosure details surgical stapling apparatus with reloads including cable driven drive beams supported on handle assemblies. These cable driven drive beams advantageously provide end effectors of the reloads with increased articulation (e.g., up to 90 degrees) relative to the handle assemblies without increased firing force for advancing the drive beams (e.g., I-beam) and sleds through the end effectors.

According to one aspect of the disclosure, a reload for a surgical stapling apparatus includes a shaft assembly and an end effector secured to the shaft assembly. The end effector includes an anvil assembly, a cartridge assembly, and a firing assembly. The firing assembly includes a drive beam and a carriage. The drive beam and the carriage are coupled together by a firing cable and a retraction cable that move the drive beam through the end effector as the carriage moves through the shaft assembly.

In aspects, the firing cable may include a first end portion coupled to the carriage and a second end portion coupled to the drive beam. The retraction cable may include a first end portion coupled to the carriage and a second end portion coupled to the drive beam. The drive beam may include a vertical wall that defines a cable conduit therethrough. The cable conduit may be configured to enable portions of the firing cable to slide therethrough as the carriage moves relative to the shaft assembly. The carriage may include a rib supported on an outer surface of the carriage. The rib may define a first aperture for coupling the first end portion of the firing cable to the carriage and a second aperture for coupling the first end portion of the retraction cable to the carriage. The firing cable may be directed around a first pulley supported on a proximal end portion of the shaft assembly and a second pulley supported on a distal end portion of the end effector. The second pulley may be supported in the cartridge assembly.

In aspects, the reload may further include a mounting assembly that couples a proximal end portion of the end effector to a distal end portion of the shaft assembly. The mounting assembly may support pulley pins. The pulley pins may support guide pulleys that enable the firing and retracting cables to be redirected in a lateral direction as the end effector articulates relative to the shaft assembly.

In aspects, the reload may include a plurality of additional pulleys supported in the shaft assembly to direct the firing and retracting cables through cable channels defined in the shaft assembly as the carriage moves through a carriage channel defined in the shaft assembly.

According to one aspect, this disclosure is directed to a surgical stapling apparatus. The surgical stapling apparatus includes a housing assembly, an adapter assembly extending from the housing assembly, and a reload selectively attachable to the adapter assembly. The reload supports an end effector on a distal end portion of the reload. The reload includes a firing assembly including a drive beam and a carriage. The drive beam and the carriage are coupled together by a firing cable and a retraction cable that move the drive beam through the end effector as the carriage moves through the reload.

In aspects, the drive beam may include a vertical wall that defines a cable conduit therethrough. The cable conduit may be configured to enable portions of the firing cable to slide therethrough as the carriage moves through the reload. The firing cable may be directed around a first pulley supported on a proximal end portion of the reload and a second pulley supported on a distal end portion of the reload. The second pulley may be supported in a cartridge assembly of the end effector.

In aspects, the surgical stapling apparatus may further include a mounting assembly that couples a proximal end portion of the end effector to a distal end portion of a shaft assembly of the reload.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate aspects of the disclosure and, together with a general description of the disclosure given above, and the detailed description of the aspect(s) given below, explain the principles of the disclosure, wherein:

FIGS. 1 and 2 are perspective views of manual and powered surgical stapling apparatus, each surgical stapling apparatus including a reload having an end effector, the end effector shown in an open position in accordance with the principles of the disclosure;

FIG. 4 is an enlarged, perspective view of the indicated area of detail shown in FIG. 3;

FIG. 5 is an enlarged, bottom perspective view of the reload of FIG. 3;

DETAILED DESCRIPTION

Figure 3:
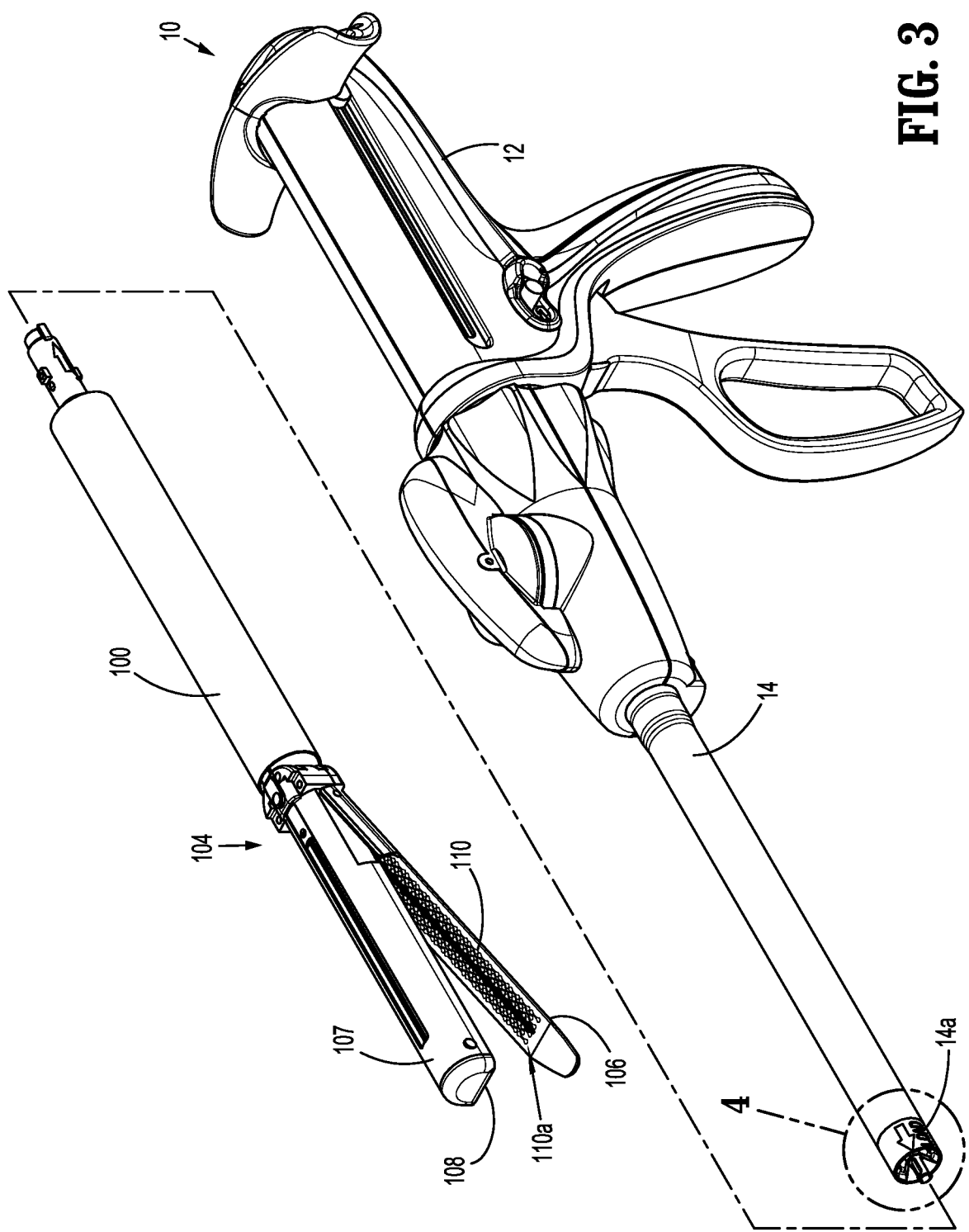
FIG. 3 is an enlarged, perspective view of the manual surgical stapling apparatus of FIG. 1, the reload of the manual surgical stapling apparatus shown separated from a handle assembly of the manual surgical stapling apparatus.
Figure 6:
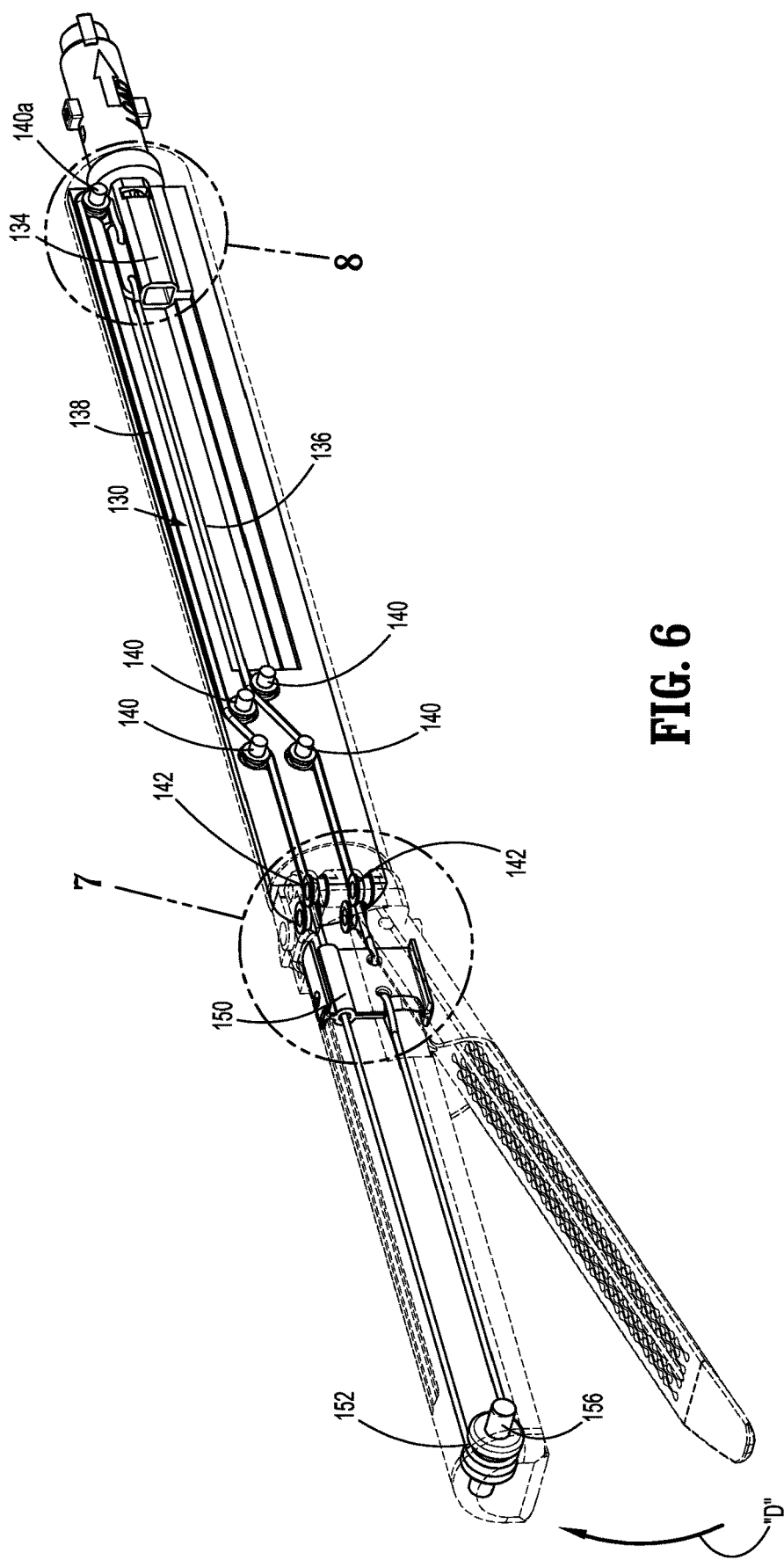
FIG. 6 is an enlarged, top perspective view of the reload of FIG. 3 with portions thereof shown in phantom for clarity.
Figure 7:
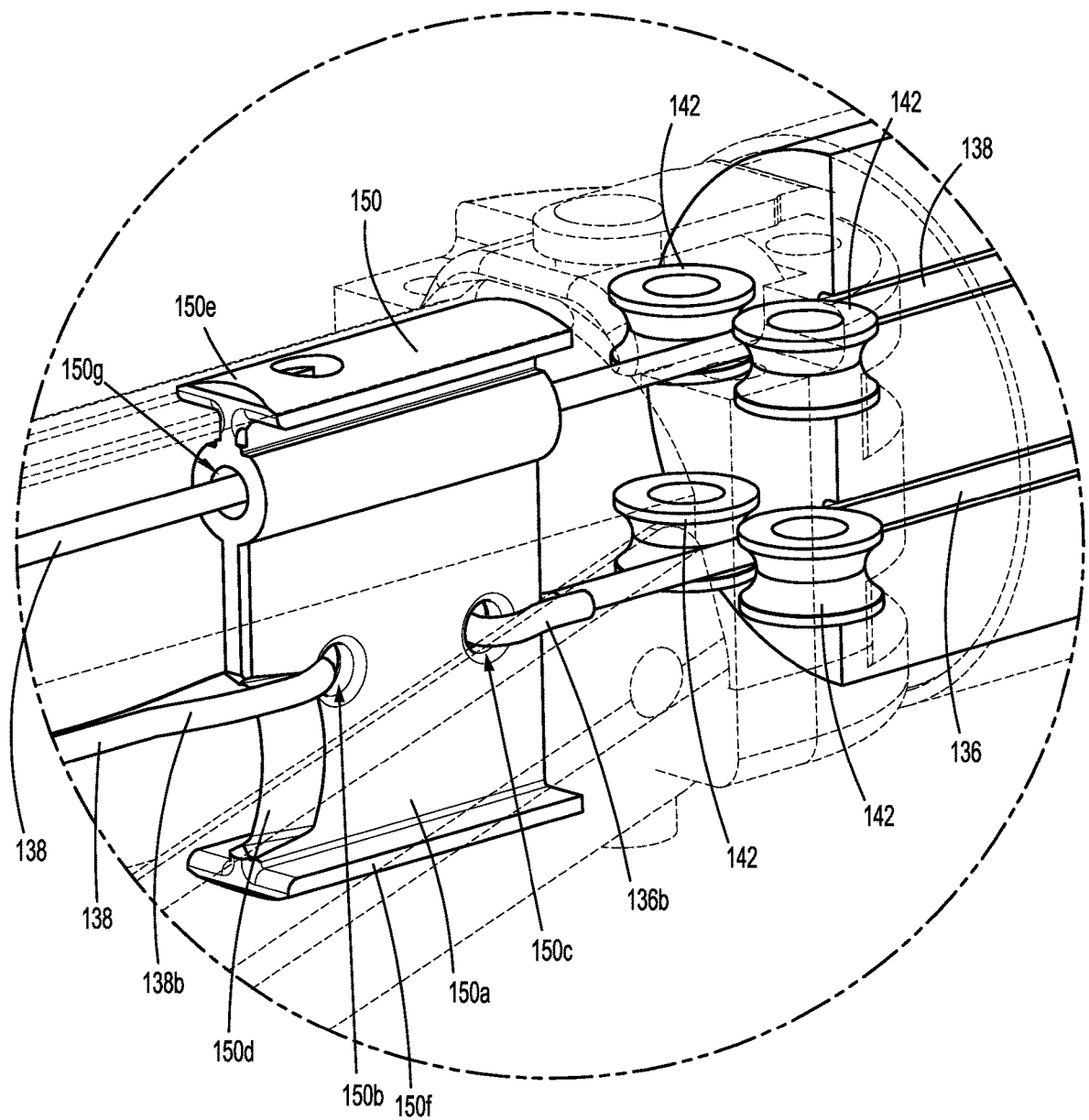
FIGS. 7 and 8 are enlarged, perspective views of the indicated areas of detail shown in FIG. 6.
Figure 8:
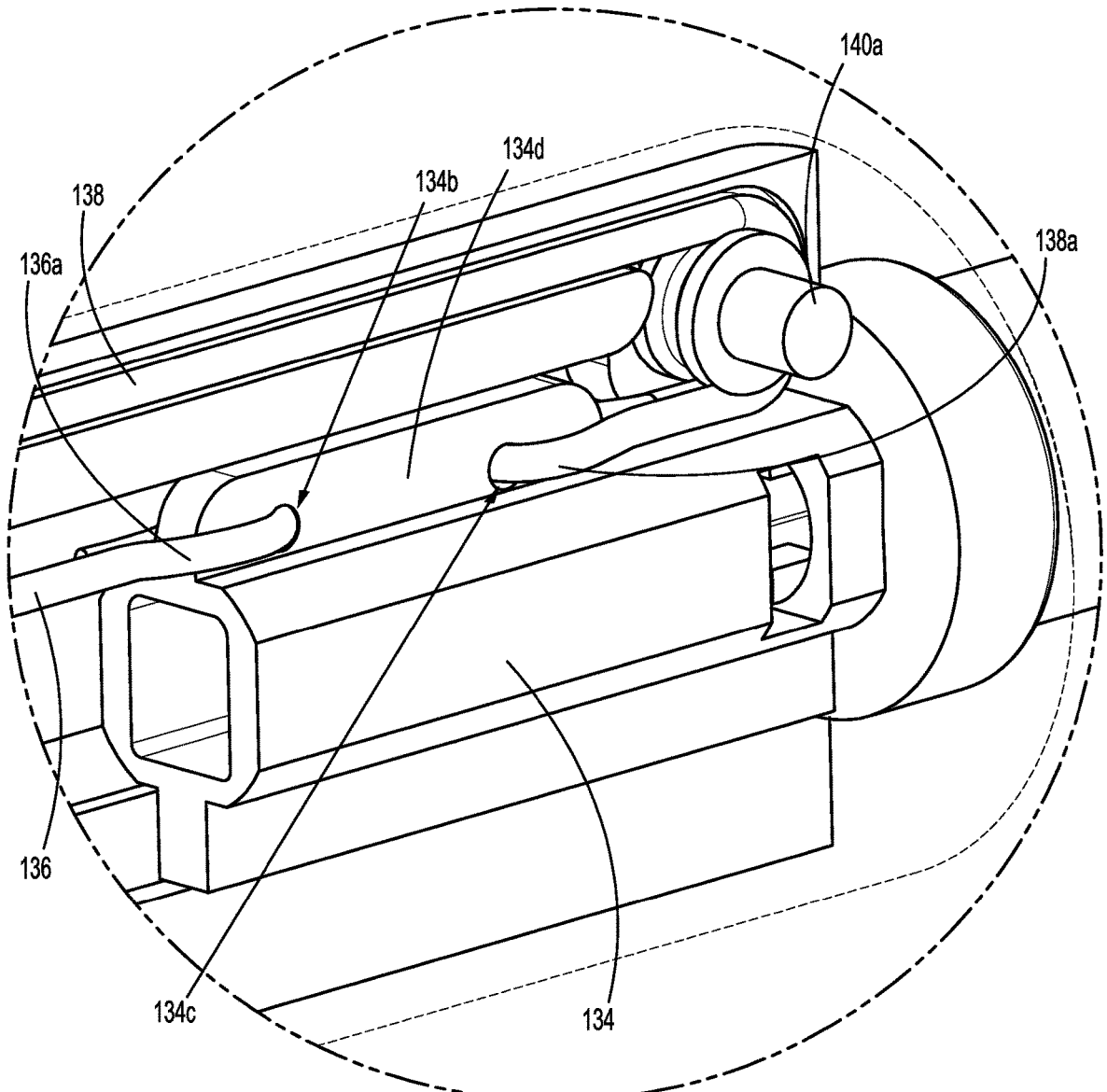

Aspects of the disclosed surgical stapling apparatus are described in detail with reference to the drawings, in which like reference numerals designate identical or corresponding elements in each of the several views. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. In addition, directional terms such as front, rear, upper, lower, top, bottom, and the like are used simply for convenience of description and are not intended to limit the disclosure attached hereto. As used herein, the term "endoscopic" is used generally used to refer to endoscopic, laparoscopic, arthroscopic, and/or any other procedure conducted through a small diameter incision or cannula.

As used herein, the terms parallel and perpendicular are understood to include relative configurations that are substantially parallel and substantially perpendicular up to about + or −10 degrees from true parallel and true perpendicular.

In the following description, well-known functions or constructions are not described in detail to avoid obscuring the present disclosure in unnecessary detail.

Further, although the surgical stapling apparatus are generally shown and described herein in connection with a linear surgical stapling system for brevity, the disclosed surgical stapling apparatus can include any powered, manual, or robotically-controlled surgical stapling systems such as a circular stapler, a transverse stapler, or an open stapler. For a detailed description of the structure and function of exemplary surgical stapling systems, one or more components of which may be included, or modified for use with the disclosed aspects, reference may be made to U.S. Pat. Nos. 9,713,470; 8,806,973; 8,256,656; 8,157,152; 8,070,033; 7,819,896; 7,770,774; 7,334,717; 7,128,253; 5,964,394; and 5,915,616, the entire contents of each of which are incorporated herein by reference.

With reference to FIGS. 1-5, a surgical stapling apparatus 10 of this disclosure includes a housing assembly 12 (which may include one or more handles that may be manually actuatable to fire surgical stapling apparatus 10), an adapter assembly 14 secured to housing assembly 12 and extending distally from housing assembly 12, and a reload 100 secured to adapter assembly 14 and extending distally from adapter assembly 14. Adapter assembly 14 and reload 100 define a longitudinal axis "X-X" that extends longitudinally therealong. Reload 100 may be reusable, disposable and/or include one or more reusable and/or disposable components. As seen in FIG. 2, the housing assembly may be in the form of a powered housing assembly 12' for a powered surgical stapling apparatus 10' that provides powered actuation of reload 100 via an adapter assembly 14'.

Figure 9:
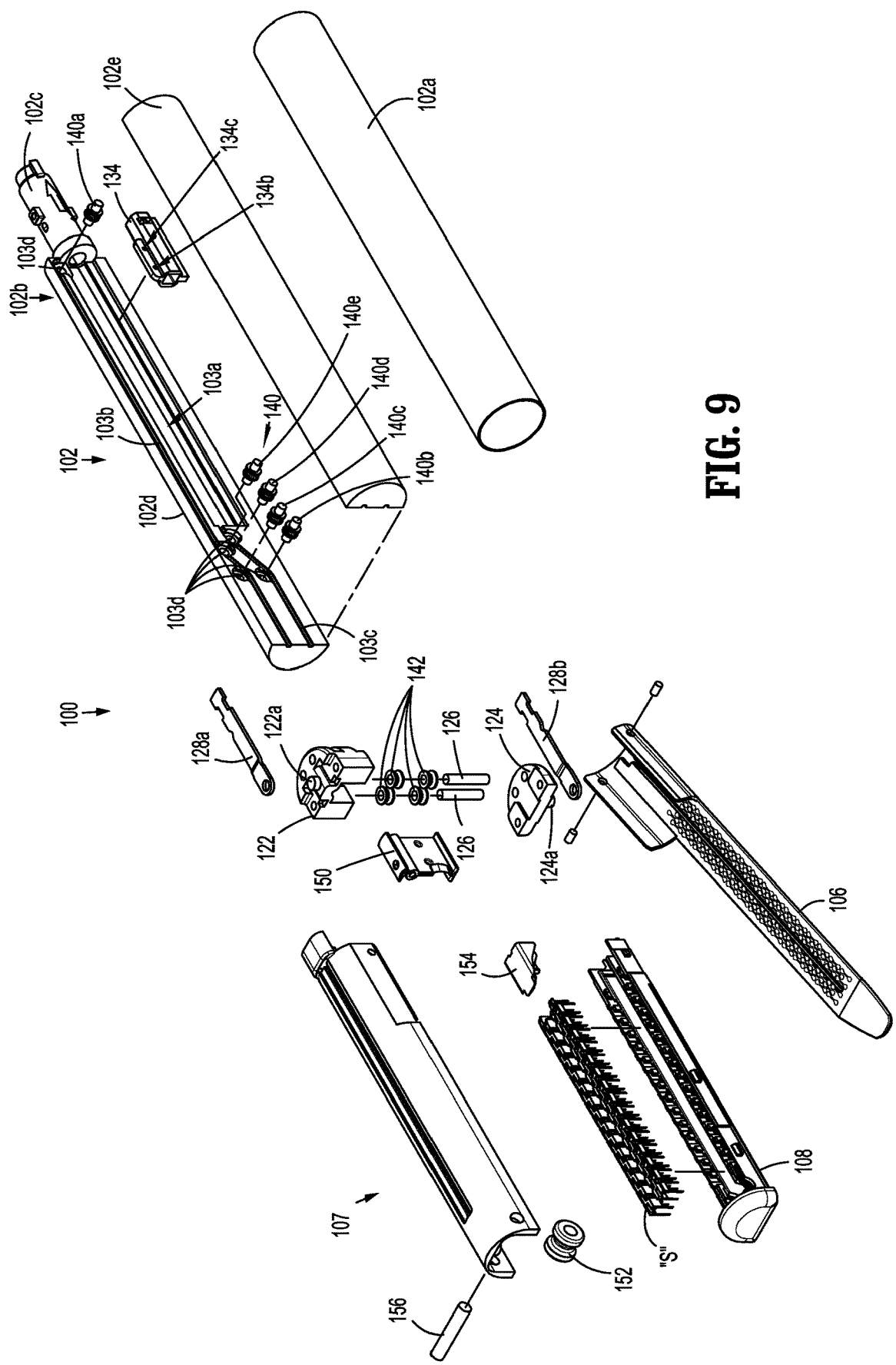
FIG. 9 is a perspective view, with parts separated, of the reload of FIG. 3.
Figure 10:
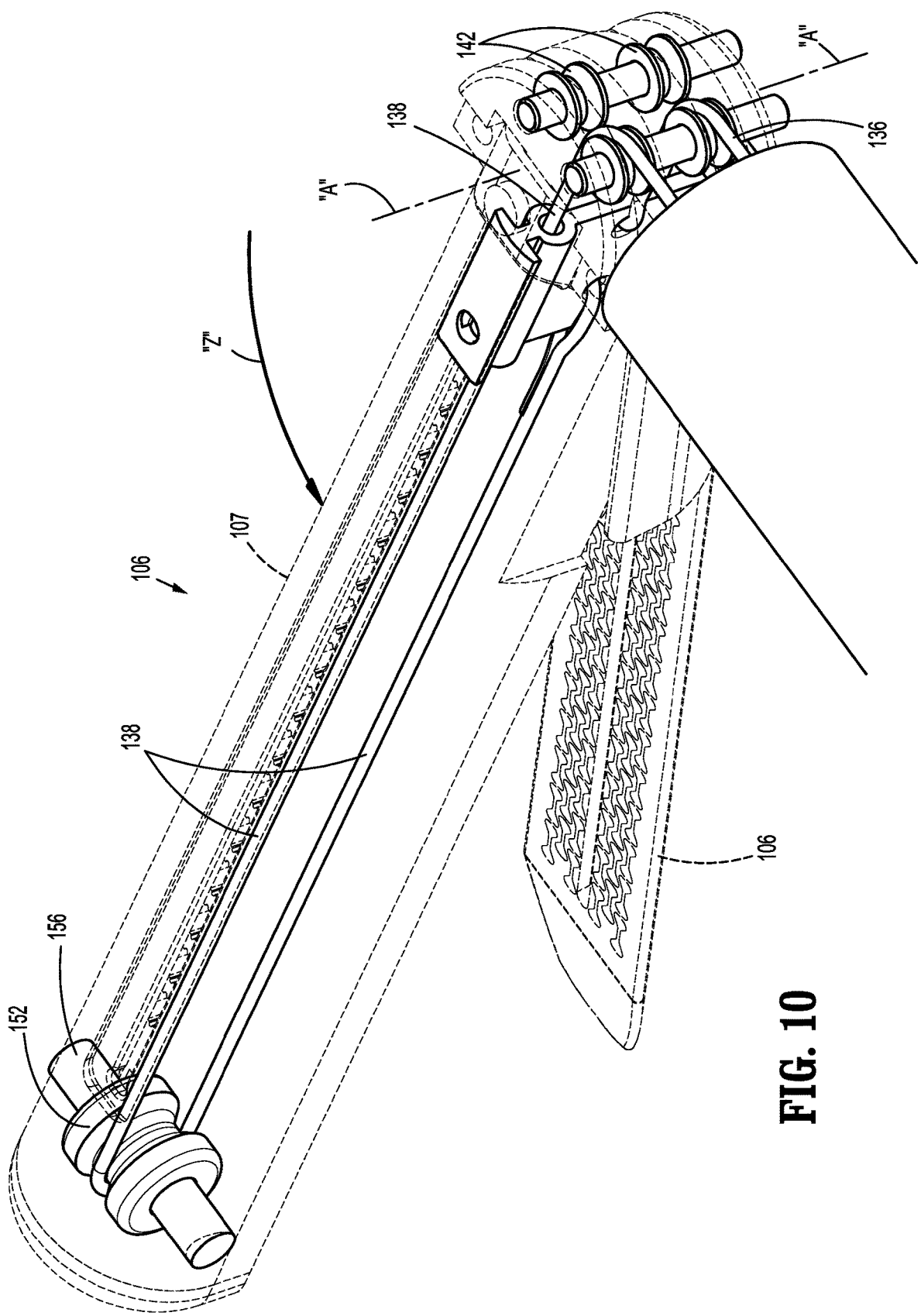
FIG. 10 is an enlarged, perspective view of a distal portion of the reload of FIG. 3 with portions thereof shown in phantom for clarity, the reload shown with an end effector thereof disposed in an articulated position.

Reload 100 of surgical stapling apparatus 10 is releasably secured to a distal end portion 14a of adapter assembly 14 and includes a shaft assembly 102 that supports an end effector 104 on a distal end portion of shaft assembly 102. End effector 104 includes an anvil assembly 106 and a cartridge assembly 107 that houses a plurality of staples (see, e.g., staples "S" shown in FIG. 9) in a plurality of rows of staple slots 108a defined in a staple cartridge 108 of cartridge assembly 104. Staple cartridge 108 may be selectively replaceable. Anvil assembly 106 includes an anvil 110 defining a plurality of rows of staple pockets 110a therein that correspond with the plurality of rows of staple slots 108a of staple cartridge 108 so that the plurality of staples "S" can be dispensed from staple slots 108a of staple cartridge 108 and formed against staple pockets 110a of anvil 110 upon a firing of surgical stapling apparatus 10.

Referring also to FIGS. 6-12, reload 100 of surgical stapling apparatus 10 supports shaft assembly 102 on a proximal end portion thereof and end effector 104 on a distal end portion thereof. End effector 104 is pivotably coupled to shaft assembly 102 by a mounting assembly 120 that enables end effector 104 to articulate relative to shaft assembly 102 about an articulation axis "AA" extending through mounting assembly 120, as indicated by arrows "Z." In particular, end effector 104 may pivot about articulation axis "A-A" from an unarticulated position (FIG. 1), aligned with longitudinal axis "X-X" of surgical stapling apparatus 10, to an articulated position (FIG. 10), in which end effector 104 may be articulated to an orthogonal position (e.g., up to 90 degrees) relative to the unarticulated position of end effector 104. Mounting assembly 120 includes an upper mounting block 122 and a lower mounting block 124 that are pinned together via pulley pins 126. Upper mounting block 122 includes an upper coupler pin 122a extending therefrom and lower mounting block 124 includes a lower coupler pin 124a depending therefrom. Upper coupler pin 122a pivotably supports an upper coupling arm 128a and lower coupler pin 124a pivotably supports a lower coupling arm 128b. Upper and lower coupling arms 128a, 128b extend from mounting assembly 120 and secure mounting assembly 120 to shaft assembly 102.

Shaft assembly 102 of reload 100 includes an outer sleeve 102a and an inner shaft assembly 102b supported within outer sleeve 102a. Inner shaft assembly 102b includes a reload connector 102c on a proximal end portion of inner shaft assembly 102b that is selectively attachable to a distal end portion 14a of adapter assembly 14 to secure reload 100 to adapter assembly 14. Inner shaft assembly 102b further includes a first shaft segment 102d and a second shaft segment 102e that are disposed in cooperative engagement with one another to support a firing assembly 130 of surgical stapling apparatus 10. First and second shaft segments 102d, 102e include mirrored structure for enabling inner shaft assembly 102b to support firing assembly 130 between first and second shaft segments 102d, 102e.

Inner shaft assembly 102b of shaft assembly 102 defines a carriage channel 103a that extends longitudinally along a proximal portion of first and second shaft segments 102d, 102e. Inner shaft assembly 102b further defines an upper cable channel 103b and a lower cable channel 103c that extend longitudinally along inner shaft assembly 102b. Inner shaft assembly 102b defines a plurality of pulley recesses 103d.

Figure 11:
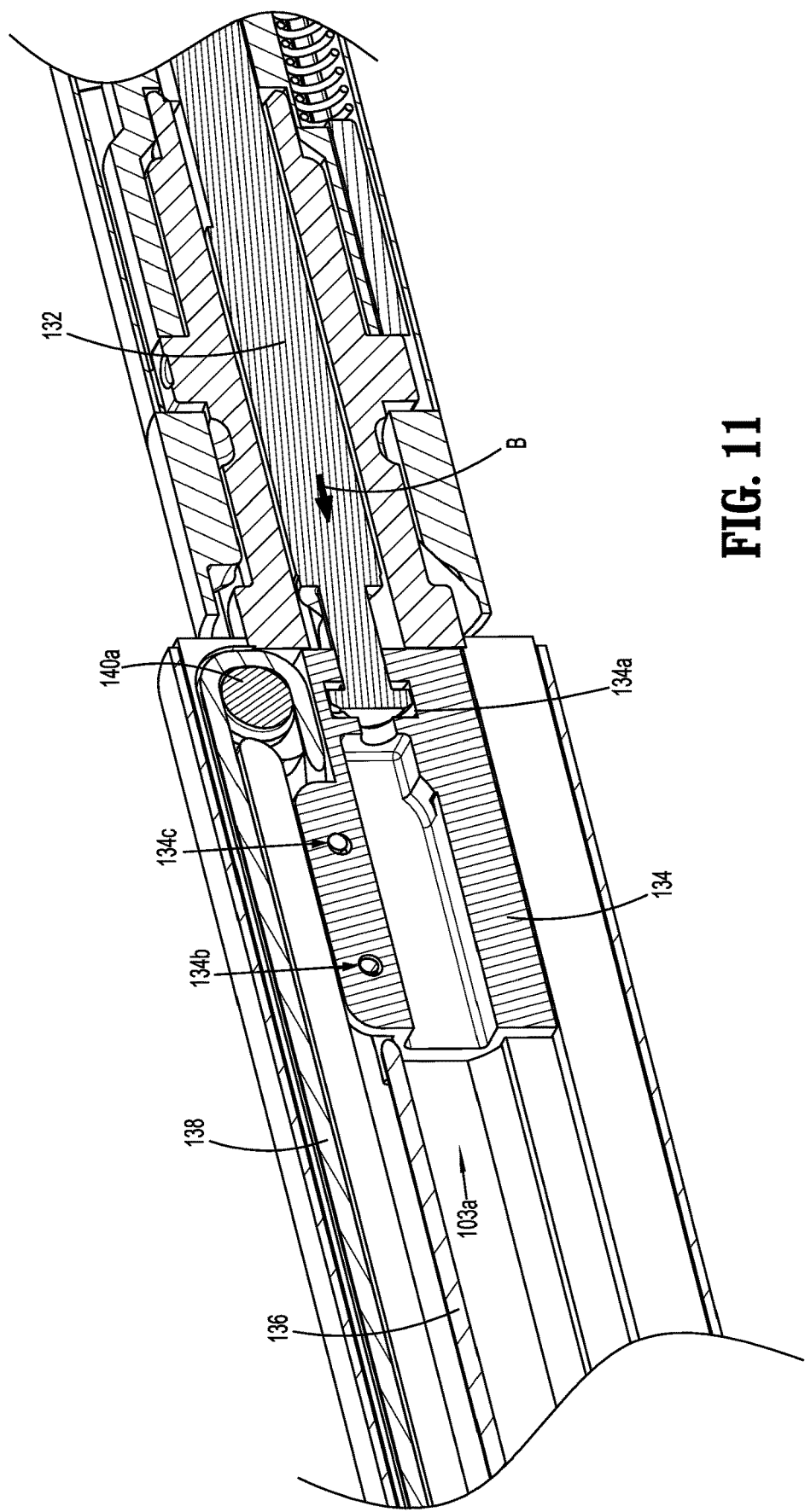
FIG. 11 is an enlarged, cross-sectional view of the manual surgical stapling apparatus as taken along section line 11-11 shown in FIG. 1.
Figure 12:
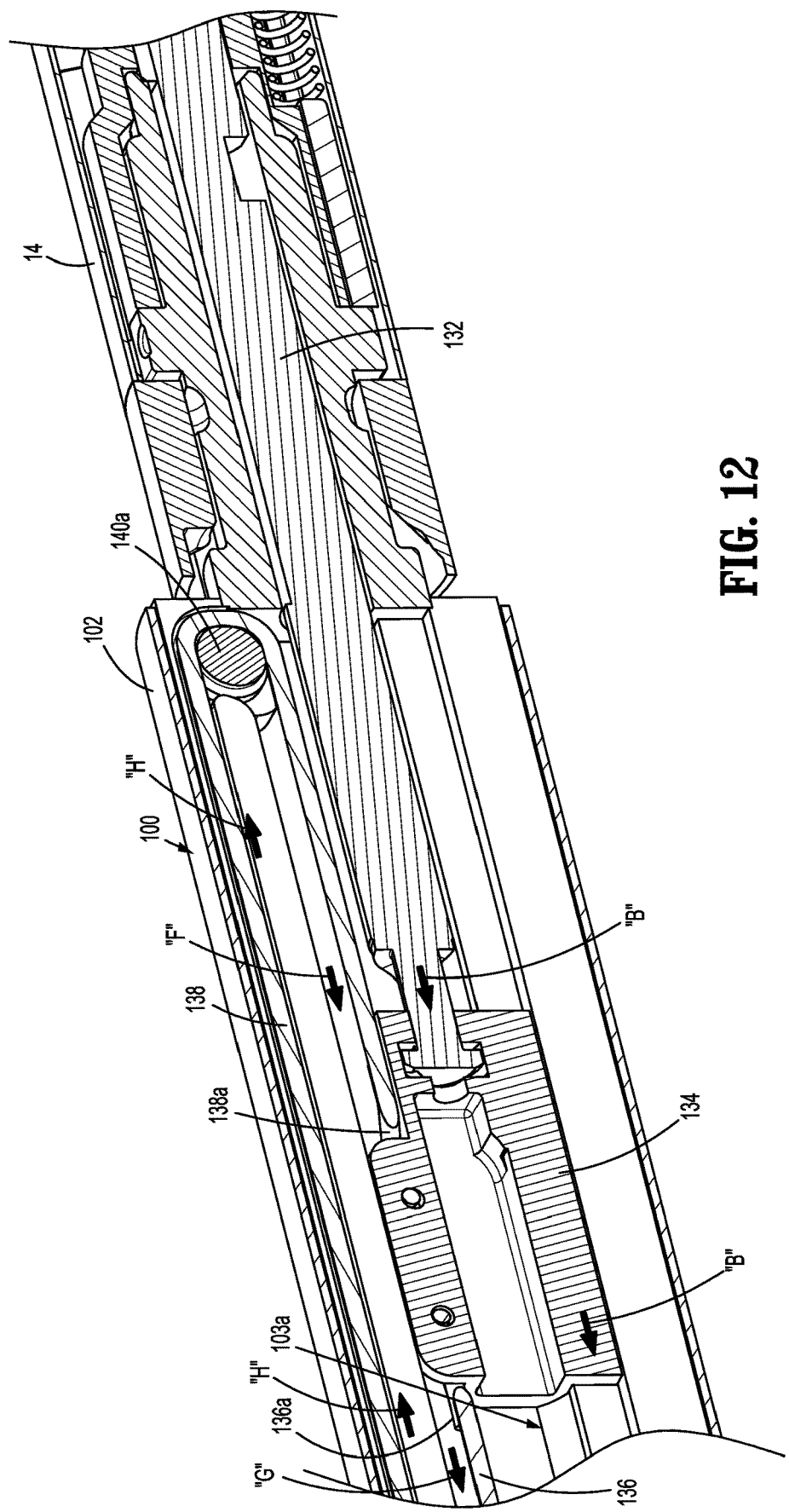
FIGS. 12 and 13 are progressive views illustrating a firing of the reload.

Firing assembly 130 of surgical stapling apparatus 10 includes a firing rod 132 that extends through adapter assembly 14 and has a proximal end portion that is operatively coupled to handle assembly 12 for selectively axially advancing firing rod 132, as indicated by arrows "B" (FIGS. 11 and 12). A distal portion of firing rod 132 is coupled to a firing rod cavity 134a defined in a proximal end portion of a carriage 134. Carriage 134 is slidably supported in carriage channel 103a of inner shaft assembly 102b and movable in response to axial movement of firing rod 132. Carriage 134 further defines distal and proximal cable apertures 134b, 134c in a rib 134d extending along an outer surface of carriage 134. Distal cable aperture 134b receives a first looped end 136a of retraction cable 136 and proximal cable aperture 134c receives a first looped end 138a of firing cable 138 therein. Firing assembly 130 further includes a plurality of cable pulleys 140 that are supported within inner shaft assembly 102b. The plurality of cable pulleys 140 includes a proximal-most pulley 140a and guide pulleys 140b, 140c, 140d, 140e that direct the retraction and firing cables 136, 138 along inner shaft assembly 102. Firing assembly 130 also includes a plurality of articulation pulleys 142 supported on pulley pins 126 of mounting assembly 120 and oriented transverse (e.g., orthogonal) to the various cable pulleys 140 to enable retraction and firing cables 136, 138 to be redirected in lateral directions as end effector 104 articulates relative to longitudinal axis "X-X".

Firing assembly 130 of surgical stapling apparatus 10 further includes a drive beam 150 supported in end effector 104 as well as a drive beam pulley 152 and a sled 154 supported in cartridge assembly 107 of end effector 104.

Figure 13:
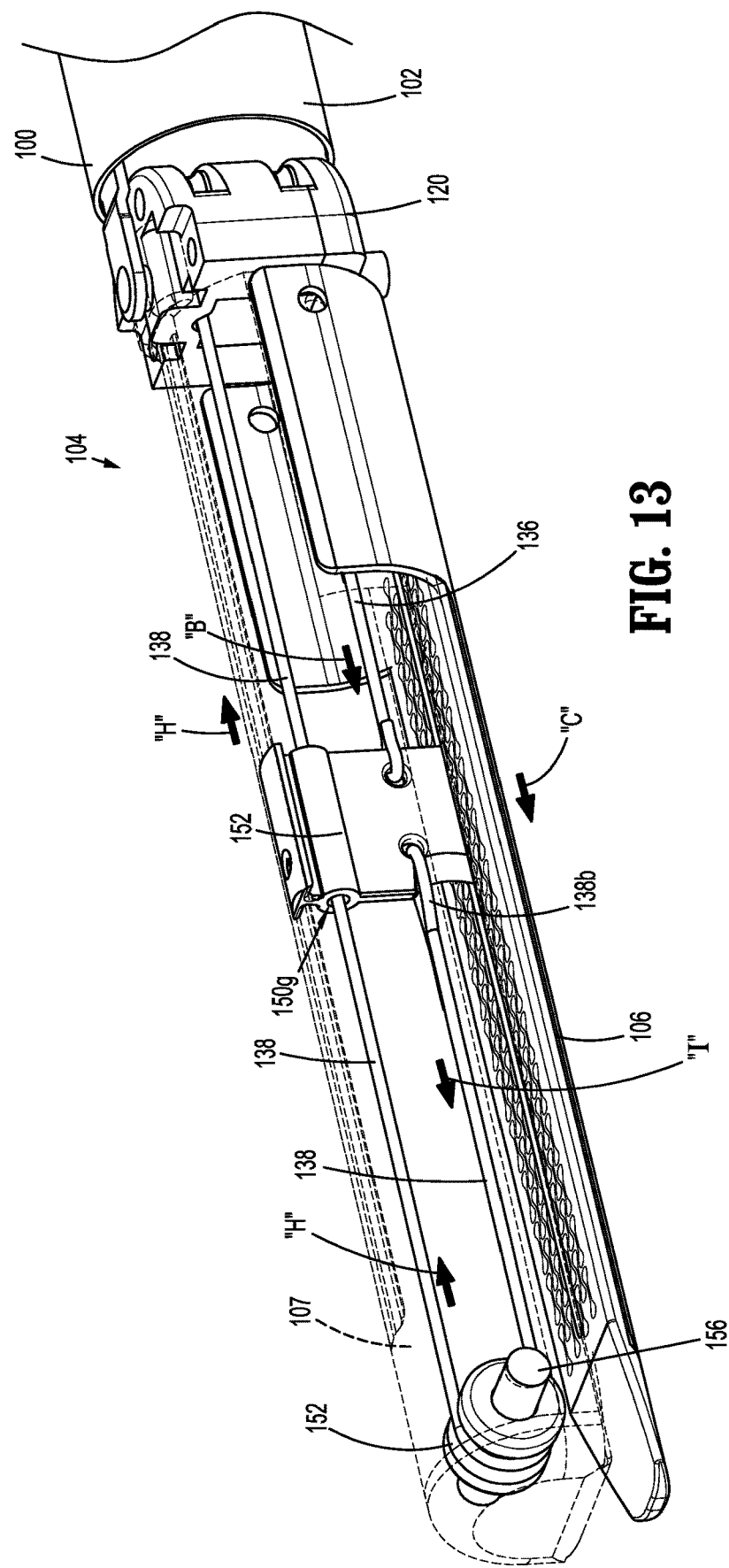

Drive beam 150 of firing assembly 130 includes a vertical wall 150a defining a distal opening 150b and a proximal opening 150c therethrough. Distal opening 150b is positioned to receive a second looped end 138a of firing cable 138 and proximal opening 150c is positioned to receive a second looped end 136b of retraction cable 136. Vertical wall 150a includes a distal knife 150d that cuts tissue as drive beam 150 is advanced distally through a knife channel 108b (FIG. 5) defined in staple cartridge 108. Drive beam 150 further includes an upper flange 150e and a lower flange 150f that slidably engage with cartridge and anvil assemblies 106, 107 of end effector 104 to move end effector 104 from an unclamped or open position (FIG. 1) to a clamped or closed position (FIG. 13), as indicated by arrow "D" (FIG. 6) for grasping, fastening, and cutting the grasped tissue as drive beam 150 and sled 154 are distally advanced through end effector 104, as indicated by arrow "C." Notably, in the clamped or closed position, the anvil and cartridge assemblies 106, 107 may be disposed in parallel or substantially parallel relation to one another. Vertical wall 150a of drive beam 150 further defines a cable conduit 150g therethrough for slidably receiving firing cable 138 through vertical wall 150a to facilitate advancement of drive beam 150 along end effector 104.

Drive beam pulley 152 is supported on a pulley pin 156 supported in cartridge assembly 107 at a distal end portion of cartridge assembly 107 and is positioned to support firing cable 138. Sled 154 is slidably advanceable through staple cartridge 108 as drive beam 150 advances through staple cartridge 108 to fire staples "S" from staple cartridge 108.

When surgical stapling apparatus 10 is fired during a surgical procedure (e.g., an endoscopic procedure), whether the end effector 104 is disposed in an articulated or unarticulated position, housing assembly 12 of surgical stapling apparatus 10 is actuated causing firing rod 132 to advance carriage 134 distally through carriage channel 103a, as indicated by arrows "B." As carriage 134 translates distally, carriage 134 draws first looped end 138a of firing cable 138 distally while driving first looped end 136a of retraction cable 136 distally, as indicated by arrows "F" and "G," respectively. Such movement of retraction and firing cables 136, 138 causes firing cable 138 to cam along proximal-most pulley 140a at the proximal end portion of end effector 104 and along drive beam pulley 152 at a distal end portion of end effector 104 so that portions of firing cable 138 travel proximally through cable conduit 150g of drive beam 150, as indicated by arrows "H." Meanwhile, other portions of firing cable 138 travel distally, as indicated by arrows "I," such that the second looped end 138b of firing cable 138 draws drive beam 150 distally through end effector 104, driving sled 154 distally to fire staples "S" and cutting clamped tissue with distal knife 150d of drive beam 150. Advantageously, due to the cable driven nature of the drive beam 150, the firing force required to advance drive beam 150 is the same or substantially the same in the articulated and unarticulated positions of end effector 104.

Securement of any of the components of the presently disclosed apparatus may be effectuated using known securement techniques such welding, crimping, gluing, fastening, etc.

The various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary aspects, and that the description, disclosure, and figures should be construed merely as exemplary of particular aspects. It is to be understood, therefore, that the present disclosure is not limited to the precise aspects described, and that various other changes and modifications may be effected by one skilled in the art without departing from the scope or spirit of the disclosure. Additionally, the elements and features shown or described in connection with certain aspects may be combined with the elements and features of certain other aspects without departing from the scope of the present disclosure, and that such modifications and variations are also included within the scope of the present disclosure. Accordingly, the subject matter of the present disclosure is not limited by what has been particularly shown and described.

What is claimed is:

1. A reload for a surgical stapling apparatus, the reload comprising:
    a shaft assembly; and
    an end effector secured to the shaft assembly and including:
        an anvil assembly;
        a cartridge assembly; and
        a firing assembly including a drive beam and a carriage, the drive beam and the carriage coupled together by a firing cable and a retraction cable that move the drive beam through the end effector as the carriage moves through the shaft assembly, wherein the drive beam includes a vertical wall that defines a cable conduit therethrough the cable conduit configured to enable portions of the firing cable to slide therethrough as the carriage moves relative to the shaft assembly.

2. The reload of claim 1, wherein the firing cable includes a first end portion coupled to the carriage and a second end portion coupled to the drive beam.

3. The reload of claim 2, wherein the retraction cable includes a first end portion coupled to the carriage and a second end portion coupled to the drive beam.

4. The reload of claim 1, wherein the carriage includes a rib supported on an outer surface of the carriage, the rib defining a first aperture for coupling the first end portion of the firing cable to the carriage and a second aperture for coupling the first end portion of the retraction cable to the carriage.

5. The reload of claim 4, wherein the firing cable is directed around a first pulley supported on a proximal end portion of the shaft assembly and a second pulley supported on a distal end portion of the end effector.

6. The reload of claim 5, wherein the second pulley is supported in the cartridge assembly.

7. The reload of claim 6, further comprising a mounting assembly that couples a proximal end portion of the end effector to a distal end portion of the shaft assembly.

8. The reload of claim 7, wherein the mounting assembly supports pulley pins, the pulley pins supporting guide pulleys that enable the firing and retracting cables to be redirected in a lateral direction as the end effector articulates relative to the shaft assembly.

9. The reload of claim 8, further comprising a plurality of additional pulleys supported in the shaft assembly to direct the firing and retracting cables through cable channels defined in the shaft assembly as the carriage moves through a carriage channel defined in the shaft assembly.

10. A surgical stapling apparatus, comprising:
    a housing assembly;
    an adapter assembly extending from the housing assembly; and
    a reload selectively attachable to the adapter assembly, the reload supporting an end effector on a distal end portion of the reload, the reload including:
        a firing assembly including a drive beam and a carriage, the drive beam and the carriage coupled together by a firing cable and a retraction cable that move the drive beam through the end effector as the carriage moves through the reload, wherein the drive beam includes a vertical wall that defines a cable conduit therethrough the cable conduit configured to enable portions of the firing cable to slide therethrough as the carriage moves through the reload.

11. The surgical stapling apparatus of claim 10, wherein the firing cable includes a first end portion coupled to the carriage and a second end portion coupled to the drive beam.

12. The surgical stapling apparatus of claim 11, wherein the retraction cable includes a first end portion coupled to the carriage and a second end portion coupled to the drive beam.

13. The surgical stapling apparatus of claim 10, wherein the carriage includes a rib supported on an outer surface of the carriage, the rib defining a first aperture for coupling the first end portion of the firing cable to the carriage and a second aperture for coupling the first end portion of the retraction cable to the carriage.

14. The surgical stapling apparatus of claim 13, wherein the firing cable is directed around a first pulley supported on a proximal end portion of the reload and a second pulley supported on a distal end portion of the reload.

15. The surgical stapling apparatus of claim 14, wherein the second pulley is supported in a cartridge assembly of the end effector.

16. The surgical stapling apparatus of claim 15, further comprising a mounting assembly that couples a proximal end portion of the end effector to a distal end portion of a shaft assembly of the reload.

17. The surgical stapling apparatus of claim 16, wherein the mounting assembly supports pulley pins, the pulley pins supporting guide pulleys that enable the firing and retracting cables to be redirected in a lateral direction as the end effector articulates relative to the shaft assembly.

18. The surgical stapling apparatus of claim 17, further comprising a plurality of additional pulleys supported in the shaft assembly to direct the firing and retracting cables through cable channels defined in the shaft assembly as the carriage moves through a carriage channel defined in the shaft assembly.

* * * * *